United States Patent
Mangino et al.

(10) Patent No.: US 12,350,289 B2
(45) Date of Patent: Jul. 8, 2025

(54) POLYMER AGENTS FOR CARDIOPULMONARY RESUSCITATION

(71) Applicant: VIRGINIA COMMONWEALTH UNIVERSITY, Richmond, VA (US)

(72) Inventors: Martin J. Mangino, Richmond, VA (US); Joseph Ornato, Richmond, VA (US); Wanchun Tang, Richmond, VA (US); Jennifer Bradley, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 924 days.

(21) Appl. No.: 17/599,253

(22) PCT Filed: Mar. 27, 2020

(86) PCT No.: PCT/US2020/025103
§ 371 (c)(1),
(2) Date: Sep. 28, 2021

(87) PCT Pub. No.: WO2020/205459
PCT Pub. Date: Oct. 8, 2020

(65) Prior Publication Data
US 2022/0175823 A1 Jun. 9, 2022

Related U.S. Application Data

(60) Provisional application No. 62/825,852, filed on Mar. 29, 2019.

(51) Int. Cl.
*A61K 31/765* (2006.01)
*A61K 9/00* (2006.01)
*A61K 9/08* (2006.01)
*A61P 9/10* (2006.01)

(52) U.S. Cl.
CPC .......... *A61K 31/765* (2013.01); *A61K 9/0019* (2013.01); *A61K 9/08* (2013.01); *A61P 9/10* (2018.01)

(58) Field of Classification Search
CPC ........ A61K 31/765; A61K 9/0019; A61P 9/10
See application file for complete search history.

(56) References Cited

U.S. PATENT DOCUMENTS

| | | |
|---|---|---|
| 2012/0156300 A1 | 6/2012 | Kheir et al. |
| 2012/0172781 A1* | 7/2012 | Wang ................ A61M 1/3613 604/509 |
| 2014/0363391 A1 | 12/2014 | Yannopoulos et al. |
| 2015/0031599 A1 | 1/2015 | Abuchowski et al. |
| 2016/0271161 A1 | 9/2016 | Dobson |
| 2017/0151198 A1 | 6/2017 | Mangino |

OTHER PUBLICATIONS

AxisPharm (https://axispharm.com/polyethylene-glycol-classification/), pp. 1-10 (Year: 2024).*
Ghasemi et al. EXCLI Journal 2021;20:1431-1445 (Year: 2021).*
Probst et al. (J Am Assoc Lab Anim Sci. Mar. 2006 ; 45(2): 49-52 (Year: 2006).*
Razzaque, M.A. et al. "Inhibition of Postinfarction Ventricular Remodeling by High Molecular Weight Polyethylene Glycol" J. Surg. Res. 2018, 232, 171-178 (Year: 2018).*
Yang, J. et al., "Effects of Polyethylene Glycolmzok on Postresuscitation Myocardial and Cerebral Function in a Rat Model of Cardiopulmonary Resuscitation", Critical Care Medicine, 2018.
Guo, Q. et al., "Abstract 14: Polyethylene Glycol-20k Improves Post-Resuscitation Cerebral Microcirculation in a Rat Model of Cardiac Arrest", Circulation, 2018.
Guo, Q. et al., "Abstract 16835: Effects of Polyethylene Glycol-20K on Postresuscitation Myocardial Function in a Rat Model of Cardiopulmonary Resuscitation", Circulation, 2018.

* cited by examiner

*Primary Examiner* — Andrew S Rosenthal
(74) *Attorney, Agent, or Firm* — WCF IP

(57) ABSTRACT

A method for resuscitation of the heart in a subject in need thereof, comprising administering to the subject a therapeutically effective amount of a solution comprising polyethylene glycol (PEG) having a molecular weight of 8-100 kDa is provided.

10 Claims, 6 Drawing Sheets

POLYMER AGENTS FOR CARDIOPULMONARY RESUSCITATION

FIELD OF THE INVENTION

The invention is generally related to methods for the acute resuscitation of the heart, for example after a cardiac arrest, by administering a polyethylene glycol solution.

BACKGROUND

Sudden cardiac arrest (SCA) is a major health issue concern in the United States. There are more than 356,000 out-of-hospital SCA annually; survival to hospital admission after EMS-treated SCA was 29%, but survival to hospital discharge was 10.8% among adults[1]. Epinephrine is the primary drug administered during cardiopulmonary resuscitation (CPR). Its stimulation effect of α-adrenergic receptor in vascular smooth muscle increases coronary perfusion pressure (CPP) and increases the rate of spontaneous circulation (ROSC). The use of epinephrine for SCA increased the rate of ROSC and survival to hospital admission. However, use of epinephrine was not associated with a significant difference in long-time survival or a favorable neurologic outcome. A prospective observational study using national registry data in Japan[2] showed that use of prehospital epinephrine was significantly associated with increased chance of ROSC before hospital arrival but decreased chance of survival and good functional outcomes 1 month after the event. In a randomized, double-blind trial, Perkins et al.[3] noted that among patients with SCA, the use of epinephrine resulted in a significantly higher rate of ROSC than placebo, but the rate of survival with a favorable neurologic outcome among patients in the epinephrine group was as low as the rate in the placebo group. In addition to increase CPP, Epinephrine also significantly increases the severity of PR myocardial and dysfunction[4] after resuscitation. Besides, increases in ventricular arrhythmias, impaired cerebral microcirculation and increased oxygen consumption are also reported concerns with epinephrine[5, 6].

Increased ROSC rate without or with decreased myocardial and neurologic dysfunction are the ultimate goal in CPR. Improved compositions and methods for achieving this goal are needed.

SUMMARY

The present disclosure provides for early and rapid vital organ protection during cardiopulmonary resuscitation. As demonstrated herein, preventing cell swelling with cell impermeants during CPR significantly reduces the severity of post-resuscitation myocardial and cerebral dysfunction and improves survival.

An aspect of the present disclosure provides a method for resuscitation of the heart in a subject in need thereof, comprising administering to the subject a therapeutically effective amount of a solution comprising polyethylene glycol (PEG) having a molecular weight of 8-100 kDa. In some embodiments, the PEG has a molecular weight of 20 kDa. In some embodiments, the solution also contains 0.1-10% of a smaller PEG polymer weighing 1-10 kDa that blocks intravascular red blood cell sedimentation. In some embodiments, the solution comprises 5-30% PEG. In some embodiments, the solution is administered intra-arterially, intravenously, or intra-osseosly. In some embodiments, the solution is administered to the femoral artery. In some embodiments, the solution is administered at a rate of less than 5% estimated blood volume per minute. In some embodiments, the solution is administered for 1-10 minutes. In some embodiments, the solution is administered during and/or after the administration of cardiopulmonary resuscitation (CPR). In some embodiments, epinephrine is not co-administered to the subject. In some embodiments, the subject suffers from one or more of cardiac arrest, myocardial infarction, cardiogenic shock, and non-cardiogenic shock.

DETAILED DESCRIPTION

The strategy of cardiopulmonary resuscitation (CPR) has focused on early defibrillation, more effective chest compression, and more recently, post-resuscitation management including therapeutic hypothermia. Embodiments of the disclosure provide a missing link in the current strategy of acute resuscitation of the heart: active protection of vital organs, e.g. during global myocardial ischemia of cardiac arrest and subsequent reperfusion of resuscitation. As used herein, the term "cardiac arrest" refers to all types of cardiac arrest, including ventricular fibrillation, asystole, and pulseless electrical activity.

Cells swell in response to ischemia and reperfusion because of the failure of energy-dependent cell volume control mechanisms. Hydropic degeneration from energy failure damages membrane and mitochondrial structures, which may lead to cell death. Swelling of parenchymal cells can also compress local capillaries, leading to further reductions in capillary flow and oxygen delivery causing a self-amplifying cycle. Tissue and cell swelling during resuscitation can cause the "no reflow phenomenon", which limits positive resuscitation outcomes and amplifies the ischemic cycle in the myocardium and other tissues dependent on myocardial blood flow and oxygen delivery, especially the brain.

Figure 6:
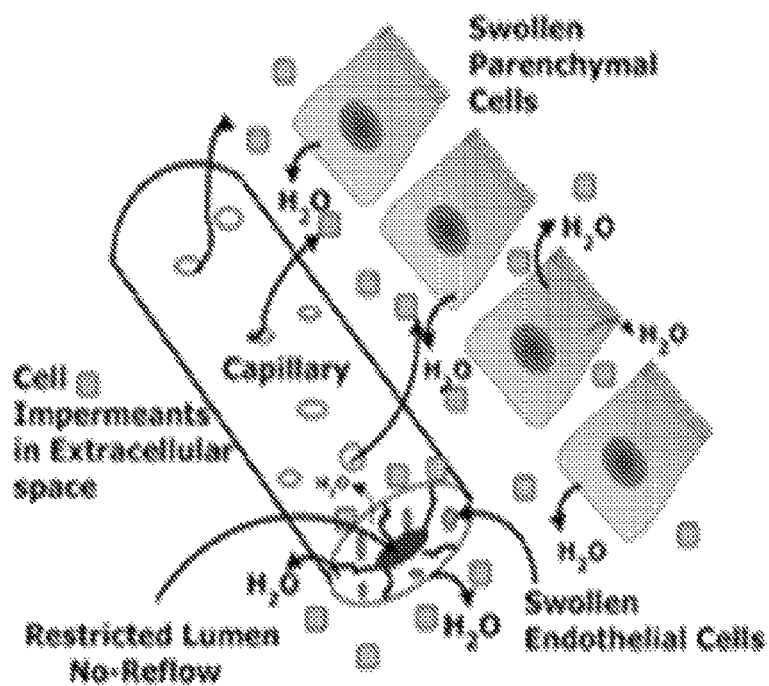
FIG. 6. Exemplary illustration of cell impermeant molecules osmotically holding water outside the cell.

Embodiments of the disclosure provide a cell impermeant solution to increase the tolerance of vital organs, including the heart and brain, to ischemia and reperfusion injuries such as during cardiac arrest and CPR, by preventing metabolic cell and tissue swelling during resuscitation. As demonstrated herein, polyethylene glycol (PEG) possesses unique osmotic reflection coefficients that establish multiple osmotic gradients in the microcirculation to rapidly and non-energetically transfer isotonic fluid away from the interior of the ischemic cell and into the capillary space. This prevents hydropic degeneration of the myocytes, decompresses the microcirculation, and reloads the myocardial capillaries to drive capillary perfusion and limit or reverse accumulation of oxygen debt during CPR. FIG. 6 shows how cell impermeant molecules as described herein can passively reverse this effect by osmotically holding water outside the cell.

Without being bound by theory, it is contemplated that PEG reduces metabolic cell and tissue swelling of the heart caused by ischemia and reperfusion and consequently improves myocardial and cerebral microcirculatory flow and enhances oxygen transfer. PEG may also protect the endothelial glycocalyx following ischemia and reperfusion, which reduces myocardial and cerebral vascular permeability and secondary cellular inflammatory responses (FIG. 6). Capillary flow and tissue water movements may be visualized with imaging techniques in the heart and brain. The degradation and repair of the glycocalyx can be monitored in the heart using biochemical metabolite tracer, immunohistochemical analysis techniques, and in-situ MALDI imaging. The Example set forth herein shows that PEG improves myocardial and cerebral function and duration of survival after cardiac arrest and resuscitation, thus providing a means of active protection of the heart and brain.

Repeating units of ethylene glycol (polyethylene glycol-PEG) can range in size from 100-8,000,000 Daltons. Polymers above 400 are nontoxic to animals and sizes above 500 are generally impermeant to cells. Polymers above 80,000 are generally confined to the capillary space where they act as colloids. Polymers of PEG between 20,000 and over 35,000 are still cell impermeants but their variable permeability to the capillary gives them some variable oncotic strength. PEG-20k (20,000 MW) has both impermeant and colloidal properties, as it distributes about ⅓ outside the capillary into the interstitial space (impermeant actions) and about ⅔ inside of the capillary where it has oncotic actions. Thus, PEG-20k is a true hybrid molecule possessing both impermeant and oncotic actions because of its size and molecular radius.

A cell impermeant is a molecule that cannot cross cell membranes, usually because the molecule is too large, too charged, or a combination of the two. Cell impermeants are not necessarily colloids but colloids are cell impermeants.

An oncotic agent is a molecule that exerts oncotic pressure, or colloid osmotic pressure, that pulls fluid into the circulatory system. It is the opposing force to capillary filtration pressure and interstitial colloidal osmotic pressure that balances out the tendency for fluid to leak out of the capillaries. In other words, the oncotic pressure tends to pull fluid into the capillaries. Loss of oncotic pressure and an increase in filtration across the capillary, results in excess fluid buildup in the tissues (edema). The large majority of oncotic pressure in capillaries is generated by the presence of high quantities of albumin which constitute approximately 80% of the total oncotic pressure exerted by blood plasma on interstitial fluid, but is lost with sudden reduction in blood volume. By definition, oncotic agents are confined to the capillary or intra-vascular space where they can restore sufficient oncotic pressure to maintain circulation of red blood cells that remain in the vessels of an individual suffering from blood loss, trauma or shock.

Embodiments of the disclosure provide a method for resuscitation of the heart in a subject in need thereof, comprising administering to the subject a therapeutically effective amount of a solution comprising PEG. In some embodiments, the PEG has a molecular weight of 8-100 kDa. In some embodiments, the PEG has a molecular weight of 20 kDa. In some embodiments, the solution comprises PEG at a concentration of 5-30% weight/volume, e.g. about 10% weight/volume. In some embodiments, the solution also contains 0.1-10% of a smaller PEG polymer weighing 1-10 kDa that blocks intravascular red blood cell sedimentation. PEG may be dissolved in any suitable solvent such as a saline solution or Lactated Ringers (LR). The solution may be a single phase solution, a dispersion, an emulsion, or any other form physically suitable for delivery to the subject. The solution is "physiologically acceptable" in that it is suitable for injection into the subject without causing undue deleterious effects. The solution may comprise autologous blood or a blood substitute. In some embodiments, the solution comprises additional cell impermeants or oncotic agents.

The solution described herein may be administered by any suitable means such as via intra-arterial, intravenous, intraosseous, or intracardiac routes. In some embodiments, the solution is administered to the femoral artery. In some embodiments, the solution is administered through a peripheral IV. In some embodiments, the solution is administered via the upper shaft of the humorous bone (upper arm). The administration can be bolus or continuous.

The term "subject" or "patient" generally refers to any mammal, typically humans. The solutions and methods described herein also have veterinary applications including, but not limited to, companion animals and farm animals.

As used herein, the terms "effective amount," or "therapeutically effective amount" refer to a nontoxic but sufficient amount of an agent to provide the desired biological result. That result may be reduction and/or alleviation of the signs, symptoms, or causes of a disease, or any other desired alteration of a biological system, such as the reduction or inhibition of metabolic cell and tissue swelling during resuscitation. In some embodiments, administration of a solution as described herein leads to volume expansion in the aorta, which consequently increases coronary perfusion pressure and increases the rate of ROSC.

The solution described herein may be administered at a slow rate, e.g. at a rate of less than 5% estimated blood volume per minute, e.g. at a rate of about 3% estimated blood volume per minute. In some embodiments, the solution is administered for 1-10 minutes, e.g. for about three minutes. In some embodiments, the total volume of solution administered to the subject is between 250-1000 milliliters (it being recognized that the volume may generally correspondingly be higher or lower depending on the patient size).

One aspect of the disclosure provides a medical bag containing a solution as described herein connected to or provided with an arterial, venous, or intra-osseous catheter or catheterization system for convenient and efficient administration in an emergency. Suitable medical/storage bags and arterial, venous, or intra-osseous catheters/lines are known in the art.

The solutions and methods described herein may replace or supplement the use of intravenous and intra-cardiac administration of vasoconstrictors such as epinephrine which has significant side effects and much poorer outcomes. The methods described may also replace or supplement the use of other drugs such as vasopressin or the use of other interventions such as intra-arterial REBOA catheters during CPR.

The administration of a solution as described herein may occur in the pre-hospital setting, on transport vehicles, or at the hospital or clinic (e.g. an emergency department, operating room, intensive care unit, or bedside) or in any setting where the coronary perfusion needs to be increased or protected (e.g. after myocardial infarction, after cardiopulmonary bypass surgery, during cardiogeneic and non-cardiogenic shock). In some embodiments, the cardiac arrest is not caused by a hemorrhage or hemorrhagic shock. In some embodiments, the solution is administered during and/or after the administration of CPR. In some embodiments, the solution is administered into the femoral artery through a percutaneous access approach during the period of active CPR resuscitation. This may be continued for short times immediately after resuscitation (return to spontaneous circulation). The method for CPR can be manual, mechanical, electrical, chemical, or a combination thereof. The cardiac resuscitation can also be performed with a closed chest or with an open chest.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

Summary

Epinephrine increases the rate of return of spontaneous circulation (ROSC). However, it significantly increases the severity of postresuscitation (PR) myocardial and cerebral dysfunction and reduces the duration of survival. In the present study, we investigated the effects of polyethylene glycol-20k on coronary perfuse pressure, PR myocardial and cerebral function and duration of survival when injected into aorta in a rat model of cardiac arrest and cardiopulmonary resuscitation. In both saline groups, the CPP did not increase regardless of whether it was injected from vein or arterial side. However, arterial injection of PEG-20k significantly increased the coronary perfusion pressure compared with Saline placebo group or Saline-A group ($p<0.05$). PEG-20k has same effect with epinephrine in increasing CPP. Furthermore, postresuscitation buccal microcirculation, myocardial and cerebral function and duration of survival were significantly improved in PEG-20k group ($p<0.05$), when compared with epinephrine group ($p<0.05$). Injection of PEG-20k into the aorta during CPR increases coronary perfusion pressure to the same extent as epinephrine. However, it improves post-resuscitation myocardial and cerebral function and increases duration of survival in a rat model of cardiopulmonary resuscitation (CPR).

Materials and Methods

All animal work was conducted under a protocol approved by the Institute Animal Care and Use Committee of Virginia Commonwealth University. Animals received humane care in compliance with the Guide for the Care and Use of Laboratory Animals published by the National Institute of Health.

Animal Preparation

Male Sprague-Dawley rats weighing 450-550 g were utilized in this study. After induction of anesthesia with inhalation of $CO_2$ for about 30 seconds, the animals were anesthetized by intraperitoneal injection of pentobarbital (45 mg/kg). Additional doses (10 mg/kg) were administered when required to maintain anesthesia. After no response to stimuli, the animals were shaved. The trachea was orally intubated with a 14-G cannula mounted on a blunt needle (Abbocath-T; Abbott Hospital Products Division, North Chicago, IL, USA) with a 145-degree angled tip. End-tidal $CO_2$ was continuously monitored with a side-stream infrared $CO_2$ analyzer (Capstar-100 Carbon Dioxide Analyzer; CWE, Ardmore, PA) interposed between the tracheal cannula and the ventilator. A conventional lead II EKG was continuously monitored. Through the left external jugular vein, a PE-50 catheter (Becton Dickinson, Sparks, MD, USA) was advanced into the right atrium for measurement of right atrial pressures. A 3-F catheter (Model C-PMS-301J; Cook Critical Care, Bloomington, IN, USA) was advanced through the right external jugular vein into the right ventricle. For blood pressure measurements within the descending aorta and PEG-20k administration, PE-50 catheters were advanced into the descending aorta from the left femoral artery and the right femoral artery respectively. A PE-50 catheter was advanced into the inferior vena cava from the right femoral vein for saline or epinephrine injection. A thermocouple microprobe (IT-18; Physitemp Instruments Inc., NJ, USA) was inserted into the left femoral vein and advanced to the descending aorta for measurement of blood temperature. A precurved guidewire supplied with the catheter was then advanced through the catheter into the right ventricle to induce ventricular fibrillation (VF), and placement of the guidewire was confirmed by an endocardial electrocardiograph. All catheters were flushed intermittently with saline containing 2.5 IU/ml of crystalline bovine heparin. During the experiment, the blood temperature was maintained at 37° C.±0.5° C. by a heating blanket.

Experimental Procedures

Rats were randomized into four groups: 1) PEG-20k group, 2) Epinephrine group, 3) Saline placebo group, and 4) Saline-A group: Normal saline in the same volume of PEG-20k was administered into aorta. PEG-20k (10% weight/volume, 1.8 ml) and Saline-A (normal saline 1.8 ml) group were administered after 4 minutes of precordial compression by continuous arterial infusion for 3 minutes with an infusion pump. Epinephrine (20 ug/kg, 1.8 ml) and Saline placebo (normal saline, 1.8 ml) group was administered after 4 minutes of precordial compression by continuous IV infusion for 3 minutes with an infusion pump. (GenieTouch; Kent Scientific, Torrington, CT). The investigators involved in CPR were blinded to group randomization.

Fifteen minutes prior to induction of VF, baseline measurements, buccal microcirculation measurement and echocardiography were obtained. Mechanical ventilation was established at a tidal volume of 0.60 ml/100 g of body weight, a frequency of 100 breaths/min, and $FIO_2$ of 0.21. Mechanical ventilation was discontinued after onset of VF. VF was then induced through a guide were advanced from the right jugular vein into the right ventricle. A progressive increase in 60-Hz current to a maximum of 3.5 mA was then delivered to the right ventricular endocardium. The current flow was continued for 3 minutes to prevent spontaneous defibrillation. After 6 minutes of untreated VF, precordial chest compressions, together with mechanical ventilation (tidal volume 0.60 ml/100 g body weight, frequency 100 breaths/min, $FIO_2$ 1.0), were initiated using a pneumatically driven mechanical chest compressor. Precordial chest compressions were maintained at a rate of 200/min and synchronized to provide a compression/ventilation ration of 2:1 with equal compression-relaxation for a duration of 8 minutes. Defibrillation was attempted with up to three 4-J counter shocks after 8 minutes of CPR. Return of spontaneous circulation (ROSC) was defined as the return of supraventricular rhythm with a mean aortic pressure above 50 mm Hg for 5 minutes. If ROSC was not achieved after the first defibrillation attempt, a 30-second interval of CPR was performed prior to the next defibrillation attempt (up to three attempts). After ROSC, an $FIO_2$ of 1.0 was continued for 1 hour, adjusted to 0.5 for the second hour, and 0.21 thereafter. If ROSC was not achieved, other rats would be randomly selected until achieving 6 resuscitated rats in each group.

Measurements

EKG, aortic and right atrial pressures, $EtCO_2$, and blood temperature values were continuously recorded on a personal computer-based data acquisition system supported by WINDAQ software (DATAQ, Akron, OH). CPP was calculated as the difference in time-coincident diastolic aortic and right atrial pressures that were displayed in real time.

Buccal microcirculation was measured at baseline, 1, 3, and 5 hours after ROSC using a side-stream dark-field imaging device (MicroScan; Microvision Medical, Amsterdam, the Netherlands) that had a 5× imaging objective, resulting in an on-screen magnification of 276×. Three discrete fields for each were captured with the intention to minimize motion artifacts. Microvascular images were recorded on a DVD with a DVD recorder (DMR-EZ47V; Panasonic AVC Networks, Dalian, China). Microcirculatory flow index (MFI) was measured using the method of Spronk et al[11]. The image was divided into four quadrants, and the predominant flow type (absent=0, intermittent=1, sluggish=2, normal=3) was assessed in the small vessels of each quadrant, which were less than 20 μm in diameter. The MFI score represented the average values of the four quadrants. Perfused vessel density (PVD) was quantitated based on the method of De Backer et al (24). Vessel density was calculated as the number of vessels crossing the catheters divided by the total length of the catheters. All recordings were analyzed by three independent observers blinded to the groups.

Myocardial function, including cardiac output (CO), ejection fraction (EF), and myocardial performance index (MPI), was measured at baseline, 2, 4, and 6 hours after ROSC by echocardiography (HD11XE; Philips Medical Systems, Eindhoven, the Netherlands) with a 12.5 Hz transducer. CO and EF were used to estimate myocardial contractility; MPI was used to estimate left ventricular diastolic function. All measurements were reviewed and confirmed separately by two investigators blinded to the groups.

Neurologic Deficit Score (NDS), which ranged from 0 (no observed neurologic deficit) to 500 (death or brain death), was used to evaluate neurologic function. The NDSs were examined and confirmed by two investigators blinded to treatment at 24, 48, and 72 hours after resuscitation.

Statistical Analysis

All data were presented as mean±SD. For measurements between groups, ANOVA and Bonferroni's method were used. Comparisons between time-based measurements within each group were performed with ANOVA repeated measurements. A value of p less than 0.05 was regarded as significant.

Results

Twenty-four rats were successfully resuscitated and included for analysis. There were no significant differences in body weight and baseline measurements including hemodynamic data, blood temperature, $EtCO_2$, myocardial function (EF, CO, and MPI), and buccal microcirculation (MFI and PVD) at baseline between the four groups.

Figure 1:
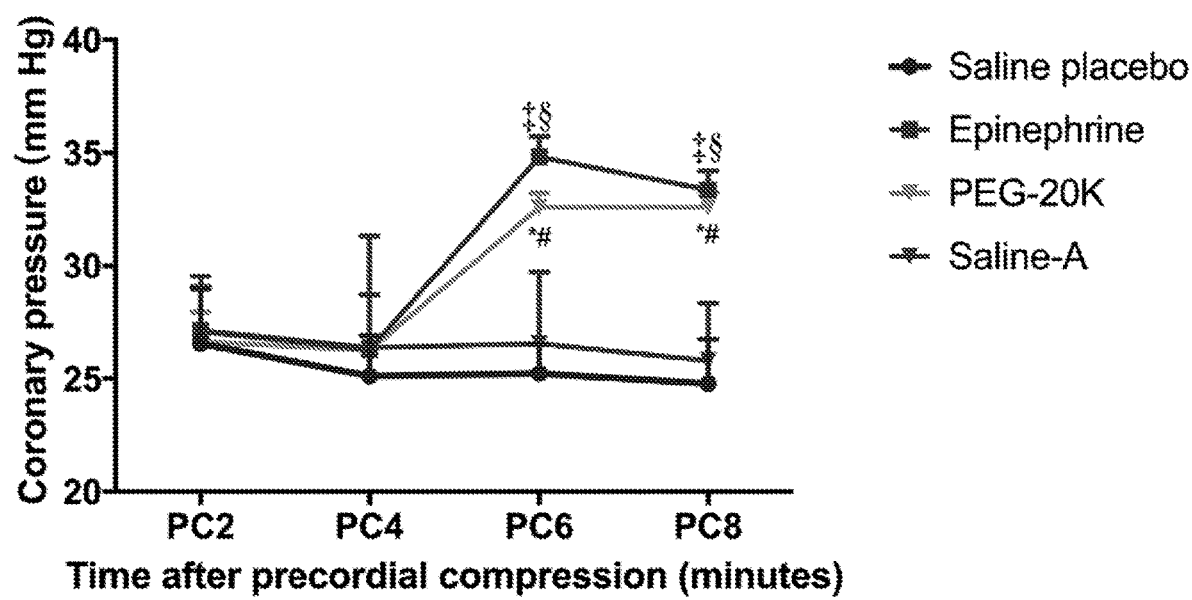
FIG. 1. Coronary perfusion pressure changes during CPR. Abbreviation: CPR, Cardiopulmonary resuscitation. *$p<0.05$ vs PEG-20k group with Saline placebo group; #$p<0.05$ vs PEG-20k group with Saline-A (intra-arterial) group; ‡$p<0.05$ vs Epinephrine group with Saline placebo group; § $p<0.05$ vs Epinephrine group with Saline-A group.

In Saline placebo group and Saline-A group, the CPP did not increase significantly when saline was injected from the vein or arterial side. However, arterial injection of PEG-20k significantly increased the coronary perfusion pressure compared with Saline placebo group or Saline-A group (p<0.05). PEG-20k had the same effect as epinephrine in increasing CPP (FIG. 1). The number of defibrillations that were required for successful conversion to a viable rhythm and restoration of spontaneous circulation were significantly higher in the epinephrine group than the saline placebo group, PEG-20k group and saline-A group (p<0.05). The duration of arrhythmia in epinephrine group was much longer than the PEG-20k group (p<0.05) (Table 1).

TABLE 1

Number of defibrillations, and arrhythmia duration.

| Group | Number of defibrillations | Arrhythmia duration |
|---|---|---|
| Saline placebo | 2.00 ± 0.89 | 9.67 ± 5.32 |
| Epinephrine | 5.50 ± 2.88†‡§ | 14.00 ± 5.35† |
| PEG-20k | 1.33 ± 0.52 | 3.17 ± 3.06 |
| Saline-A | 2.33 ± 0.82 | 10.67 ± 6.68 |

†p < 0.05 vs PEG-20k group with Epinephrine group; ‡p < 0.05 vs Epinephrine group with Saline placebo group; §p < 0.05 vs Epinephrine group with Saline-A.

Figure 2:
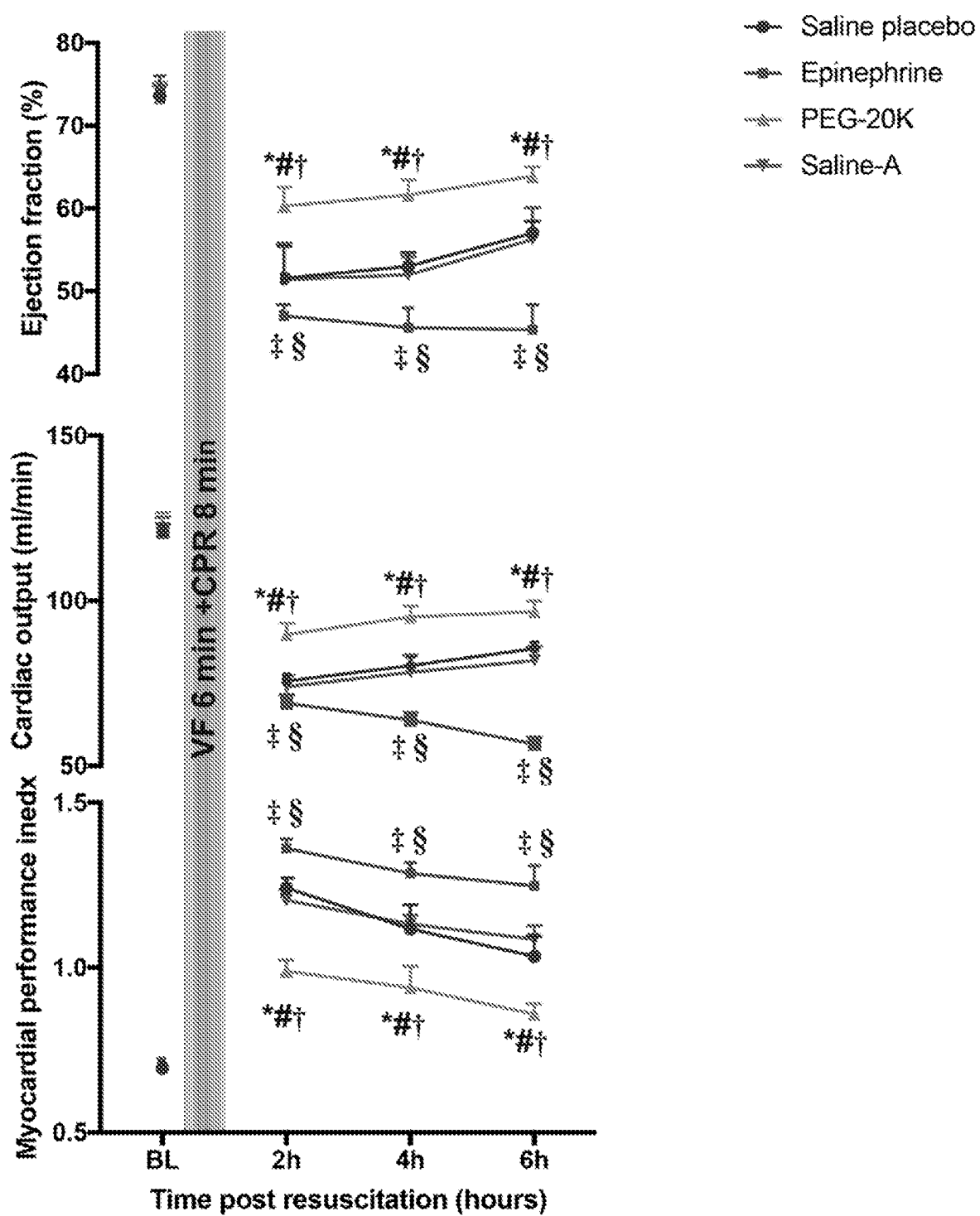
FIG. 2. Polyethylene glycol-20k improves post-resuscitation myocardial function. Abbreviation: CPR, Cardiopulmonary resuscitation; VF, Ventricular fibrillation; BL, Baseline. *$p<0.05$ vs PEG-20K group with Saline placebo group; #$p<0.05$ vs PEG-20k group with Saline-A group; †$<0.05$ vs PEG-20k group with Epinephrine group; ‡$p<0.05$ vs Epinephrine group with Saline placebo group; § $p<0.05$ vs Epinephrine group with Saline-A group.
Figure 3:
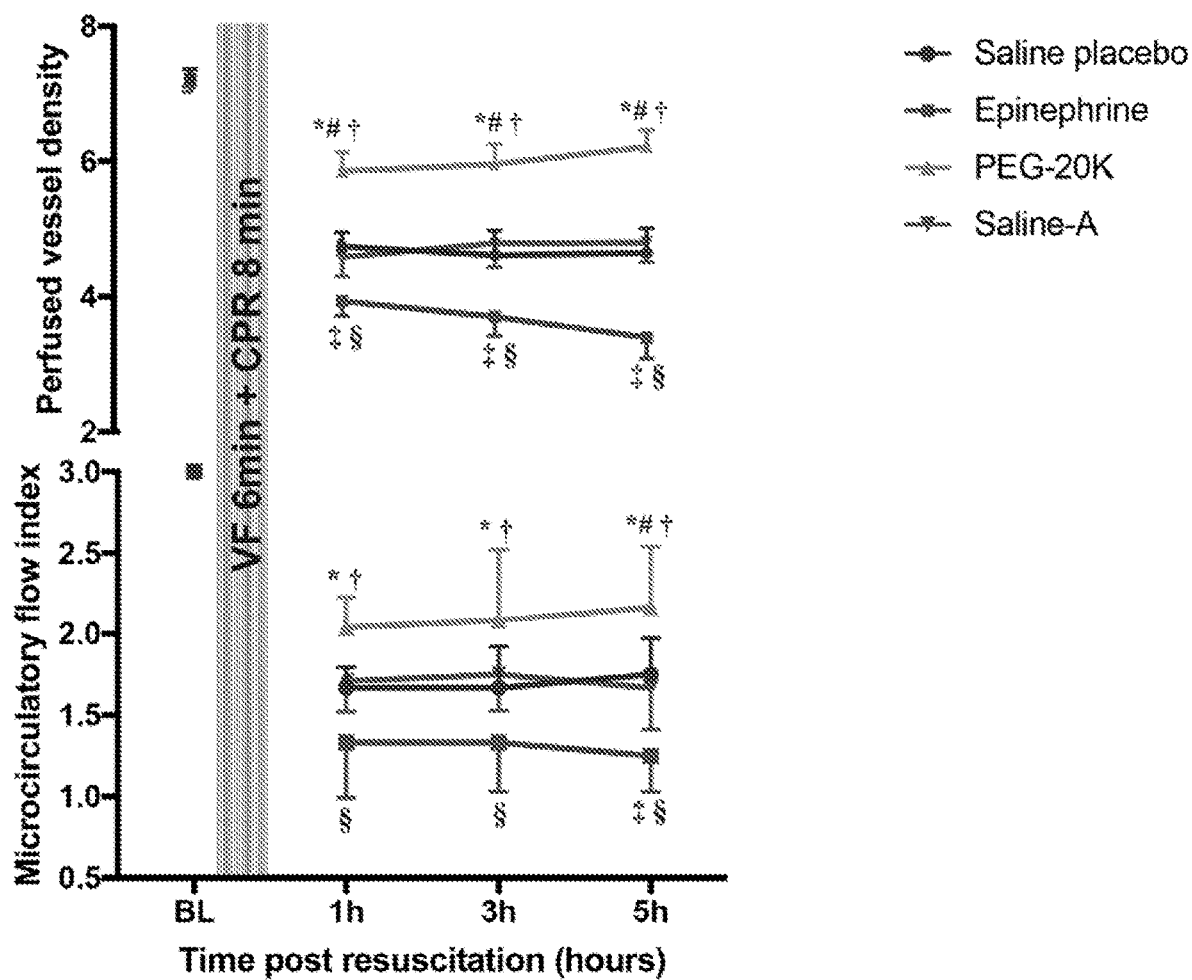
FIG. 3. Polyethylene glycol-20k improves buccal microcirculation. Abbreviation: CPR, Cardiopulmonary resuscitation; VF, Ventricular fibrillation; BL, Baseline. *$p<0.05$ vs PEG-20k group with Saline placebo group; #$p<0.05$ vs PEG-20k group with Saline-A group; †$p<0.05$ vs PEG-20k group with Epinephrine group; ‡$p<0.05$ vs Epinephrine group with Saline placebo group; § $p<0.05$ vs Epinephrine group with Saline-A group.

After resuscitation, myocardial function as measured by CO, EF, and MPI, was significantly impaired in all groups when compared with baseline. PEG-20k treatment during precordial compression significantly improved the severity of PR myocardial function when compared with the other 3 groups (p<0.05). The epinephrine increased the severity of PR myocardial dysfunction when compared with saline placebo group and saline-A group (p<0.05) (FIG. 2). Buccal microcirculation was significantly reduced after successful resuscitation in all groups compared with baseline. PEG-20k treatment also significantly increased PVD and MFI values when compared to the other 3 groups (p<0.05). However, PVD and MFI values were significantly decreased when compared with saline placebo group and saline-A group (p<0.05) (FIG. 3).

Figure 4:
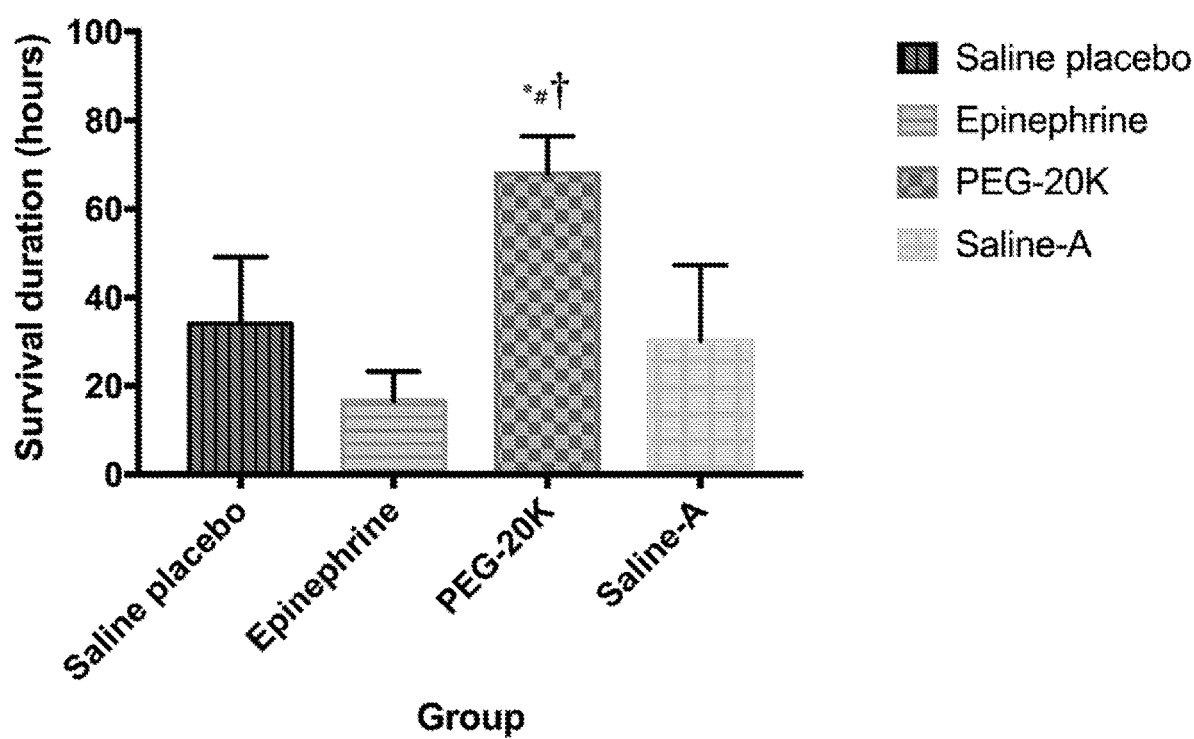
FIG. 4. Polyethylene glycol-20k improves survival duration. *$p<0.05$ vs PEG-20k group with Saline placebo group; #$p<0.05$ vs PEG-20k group with Saline-A group; †$p<0.05$ vs PEG-20k group with Epinephrine group; ‡$p<0.05$ vs Epinephrine group with Saline placebo group.
Figure 5:
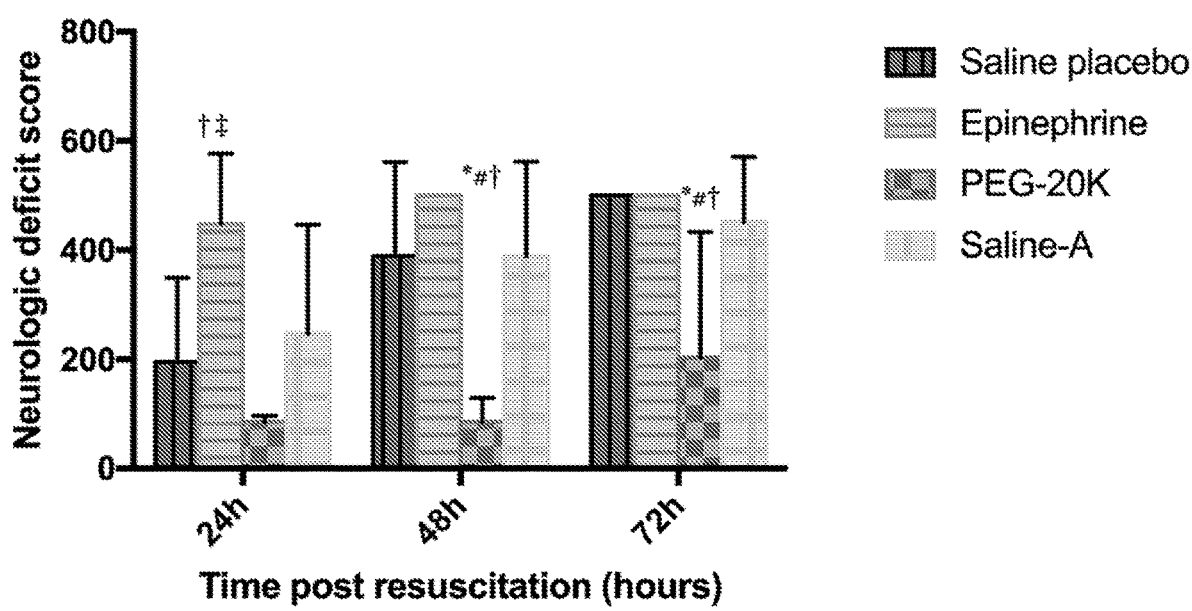
FIG. 5. Polyethylene glycol-20k improves post-resuscitation cerebral function. *$p<0.05$ vs PEG-20k group with Saline placebo group; #$p<0.05$ vs PEG-20k group with Saline-A group; †$p<0.05$ vs PEG-20k group with Epinephrine group.

Duration of survival in the animal treated with PEG-20k was significantly improved when compared with the other 3 groups (p<0.05). Four rats survived 72 hours in the PEG-20k group, no rats survived through the entire 72 hours in saline placebo group and saline-A group, and only one rat survived more than 24 hours in epinephrine group (FIG. 4). PR neurologic function was assessed by NDS. Lower NDS values were observed in the PEG-20k group compared with saline-A group and epinephrine group at 24 hours after resuscitation (p<0.05). NDS values were significantly decreased in the PEG-20k group when compared with the other 3 groups at 48 and 72 hours after resuscitation (FIG. 5). The rats treated with PEG-20k during precordial compression had significantly reduced severity of PR neurologic dysfunction when compared with the other 3 groups (p<0.05)

Discussion

The present study demonstrated that the administration of epinephrine during CPR increased the severity of myocardial and neurological dysfunction. PEG-20k injected into aorta significantly increased CPP to the same extent as epinephrine during CPR. Myocardial and cerebral function, duration of survival was also improved in the PEG-20k group post resuscitation when compared with the epinephrine group.

For successful resuscitation, a critical level of marginal myocardial blood flow must be obtained to deliver oxygen to tissues and improve the metabolic state of the myocardium.[12, 13]. CPP represents the gradient that drives blood flow through myocardial capillary beds. It is well established that higher CPP and the consequent increased myocardial flow are strongly associated with increased rate of ROSC [13, 14]. The CPP has been a golden standard of the success of resuscitation.

Epinephrine is a catecholamine that causes peripheral vasoconstriction via stimulation of α receptor but also acts on β receptors. Its α-adrenergic receptor stimulation has been shown to be the most beneficial during CPR. However, the $α_1$ adrenergic and β-adrenergic effect of epinephrine had adverse effects on outcomes. We have previously demonstrated that epinephrine increases the severity of PR myocardial dysfunction and myocardial tissue injury[5, 15-17]. Our results are also consistent with clinical trials in which epinephrine did not result in better short-term survival or hospital discharge rate[2, 3].

Because of the deleterious effects of epinephrine, the use of nonadrenergic agents such as vasopression in cardiac arrest served as an alternative or as an adjunct to epinephrine. When given at high doses, it causes vasoconstriction by directly stimulating smooth muscle Vi receptors. However, its efficacy was doubted when compared with epinephrine [18-21].

PEG-20k is a hybrid molecule which acts as colloids and has oncotic effects. It presents a greater hydrodynamic volume than would be expected from its molecular weight due to the high flexibility, hydrophilicity and the large number of water molecules coordinated by its chains. The capillary oncotic reflection coefficient for PEG-20k indicates a hybrid nature of PEG-20k[22]. After administration of PEG-20k solutions, the solutions have a significant effect on expansion of the blood volumes due to a large portion of the molecule stays behind in the capillary to exert oncotic force that draws the interstitial water into the capillary, which lead to increase coronary perfusion pressure during precordial compression.

Consistent with our previous study[10], duration of survival in the animal treated with PEG-20k group was significantly improved. NDS score representing cerebral function was decreased correspondingly. PEG-20k solutions pull isotonic fluid out of the extravascular space, thereby decompressing and filling capillaries, which improves oxygen delivery. Besides, PEG-20k solutions have an effect on the expansion of blood volumes, which leads to increased coronary perfusion pressure during precordial compression. Increased flow in carotid arteries serves to increase the cerebral perfusion pressure and bolster cerebral flow, which are associated with improved neurologic outcomes[23]. Furthermore, PEG-20k administration decreases ischemia-reperfusion injury in the heart, which will decrease the occurrence of arrhythmia, microvascular damage, myocardial stunning or cell death. Higher coronary perfusion pressure is associated with improvements in cerebral perfusion and oxygenation and may be neuroprotective[24].

Our study evaluated the effects of PEG-20k on coronary perfusion pressure during CPR and post-resuscitation myocardial and cerebral function in a rat model of cardiac arrest and resuscitation. The study demonstrated significantly increased coronary perfuse pressure during CPR and improved PR outcomes in the PEG-20k treatment group.

PEG-20k increases coronary perfusion pressure and protects cardiomyocyte function, which will increase the success rate and decrease cerebral dysfunction. PEG-20k can thus decrease post-resuscitation mortality rates after cardiac arrest.

REFERENCES

1. Benjamin E J, Virani S S, Callaway C W, Chamberlain A M, Chang A R, Cheng S, et al. Heart Disease and Stroke Statistics-2018 Update: A Report From the American Heart Association. Circulation. 2018; 137(12):e67-e492. Epub 2018/02/02. doi: 10.1161/CIR.0000000000000558. PubMed PMID: 29386200.
2. Hagihara A, Hasegawa M, Abe T, Nagata T, Wakata Y, Miyazaki S. Prehospital Epinephrine Use and Survival Among Patients With Out-of-Hospital Cardiac Arrest. JAMA. 2012; 307(11):1161-8. doi: 10.1001/jama.2012.294% J JAMA.
3. Perkins G D, Ji C, Deakin C D, Quinn T, Nolan J P, Scomparin C, et al. A Randomized Trial of Epinephrine in Out-of-Hospital Cardiac Arrest. N Engl J Med. 2018; 379(8):711-21. Epub 2018/07/19. doi: 10.1056/NEJMoa1806842. PubMed PMID: 30021076.
4. Dumas F, Bougouin W, Geri G, Lamhaut L, Bougle A, Daviaud F, et al. Is Epinephrine During Cardiac Arrest Associated With Worse Outcomes in Resuscitated Patients? Journal of the American College of Cardiology. 2014; 64(22):2360-7. doi: 10.1016/j.jacc.2014.09.036. PubMed PMID: WOS:000345962200009.
5. Sun S, Tang W, Song F, Yu T, Ristagno G, Shan Y, et al. The effects of epinephrine on outcomes of normothermic and therapeutic hypothermic cardiopulmonary resuscitation. Crit Care Med. 2010; 38(11):2175-80. Epub 2010/08/10. doi: 10.1097/CCM.0b013e3181eedad6. PubMed PMID: 20693888.
6. Burnett A M, Segal N, Salzman J G, McKnite M S, Frascone R J. Potential negative effects of epinephrine on carotid blood flow and ETCO2 during active compression-decompression CPR utilizing an impedance threshold device. Resuscitation. 2012; 83(8):1021-4. Epub 2012/03/27. doi: 10.1016/j.resuscitation.2012.03.018. PubMed PMID: 22445865.
7. Kaufman S, Kaesermann H P, Peters GJJoP. The mechanism of drinking induced by parenteral hyperoncotic solutions in the pigeon and in the rat. 1980; 301(1):91-9.
8. Parrish D, Lindell S L, Reichstetter H, Aboutanos M, Mangino M J. Cell Impermeant-based Low-volume Resuscitation in Hemorrhagic Shock: A Biological Basis for Injury Involving Cell Swelling. Ann Surg. 2016; 263(3):565-72. Epub 2015/04/29. doi: 10.1097/SLA.0000000000001049. PubMed PMID: 25915911; PubMed Central PMCID: PMCPMC4747844.
9. Plant V, Parrish D W, Limkemann A, Ferrada P, Aboutanos M, Mangino M J. Low-Volume Resuscitation for Hemorrhagic Shock: Understanding the Mechanism of PEG-20k. J Pharmacol Exp Ther. 2017; 361(2):334-40. Epub 2017/03/10. doi: 10.1124/jpet.116.239822. PubMed PMID: 28275202.
10. Yang J, Xiao Y, Quan E Y, Hu Z, Guo Q, Miao C, et al. Effects of Polyethylene Glycol-20k on Postresuscitation Myocardial and Cerebral Function in a Rat Model of Cardiopulmonary Resuscitation. Crit Care Med. 2018; 46(12):e1190-e5. Epub 2018/09/21. doi: 10.1097/CCM.0000000000003415. PubMed PMID: 30234522.
11. Spronk P E, Ince C, Gardien M J, Mathura K R, Oudemans-van Straaten H M, Zandstra D F. Nitroglycerin in septic shock after intravascular volume resuscitation. Lancet. 2002; 360(9343):1395-6. Epub 2002/11/09. PubMed PMID: 12423989.
12. Ralston S H, Voorhees W D, Babbs C F. Intrapulmonary epinephrine during prolonged cardiopulmonary resuscitation: improved regional blood flow and resuscitation in dogs. Ann Emerg Med. 1984; 13(2):79-86. Epub 1984/02/01. PubMed PMID: 6691623.
13. Paradis N A, Martin G B, Rivers E P, Goetting M G, Appleton T J, Feingold M, et al. Coronary perfusion pressure and the return of spontaneous circulation in human cardiopulmonary resuscitation. JAMA. 1990; 263(8):1106-13. Epub 1990/02/23. PubMed PMID: 2386557.
14. Halperin H R, Lee K, Zviman M, Illindala U, Lardo A, Kolandaivelu A, et al. Outcomes from low versus high-flow cardiopulmonary resuscitation in a swine model of cardiac arrest. Am J Emerg Med. 2010; 28(2):195-202. Epub 2010/02/18. doi: 10.1016/j.ajem.2009.10.006. PubMed PMID: 20159390.
15. Ristagno G, Tang W, Huang L, Fymat A, Chang Y T, Sun S, et al. Epinephrine reduces cerebral perfusion during cardiopulmonary resuscitation. Crit Care Med. 2009; 37(4):1408-15. Epub 2009/02/27. doi: 10.1097/CCM.0b013e31819cedc9. PubMed PMID: 19242339.
16. Tang W, Weil M H, Sun S, Noc M, Yang L, Gazmuri R J. Epinephrine increases the severity of postresuscitation myocardial dysfunction. Circulation. 1995; 92(10):3089-93. Epub 1995/11/15. PubMed PMID: 7586280.
17. Yang M, Hu X, Lu X, Wu X, Xu J, Yang Z, et al. The effects of alpha- and beta-adrenergic blocking agents on postresuscitation myocardial dysfunction and myocardial tissue injury in a rat model of cardiac arrest. Transl Res. 2015; 165(5):589-98. Epub 2014/12/04. doi: 10.1016/j.trsl.2014.10.012. PubMed PMID: 25468485.
18. Babar S I, Berg R A, Hilwig R W, Kern K B, Ewy G A. Vasopressin versus epinephrine during cardiopulmonary resuscitation: a randomized swine outcome study. Resuscitation. 1999; 41(2):185-92. Epub 1999/09/17. PubMed PMID: 10488942.
19. Wenzel V, Linder K H, Augenstein S, Prengel A W, Strohmenger H U, % J Storoke. Vasopressin combined with epinephrine decreases cerebral perfusion compared with vasopressin alone during cardiopulmonary resuscitation in pigs. 1998; 29(7):1462-7; discussion 7-8.
20. Stiell I G, Hebert P C, Wells G A, Vandemheen K L, Tang A S, Higginson L A, et al. Vasopressin versus epinephrine for inhospital cardiac arrest: a randomised controlled trial. Lancet. 2001; 358(9276):105-9. Epub 2001/07/21. doi: 10.1016/S0140-6736(01)05328-4. PubMed PMID: 11463411.
21. Ong M E, Tiah L, Leong B S, Tan E C, Ong V Y, Tan E A, et al. A randomised, double-blind, multi-centre trial comparing vasopressin and adrenaline in patients with cardiac arrest presenting to or in the Emergency Department. Resuscitation. 2012; 83(8):953-60. Epub 2012/02/23. doi: 10.1016/j.resuscitation.2012.02.005. PubMed PMID: 22353644.
22. Parrish D, Plant V, Lindell S L, Limkemann A, Reichstetter H, Aboutanos M, et al. New low-volume resuscitation solutions containing PEG-20k. J Trauma Acute Care Surg. 2015; 79(1):22-9. Epub 2015/06/20. doi: 10.1097/TA.0000000000000682. PubMed PMID: 26091310; PubMed Central PMCID: PMCPMC4476060.
23. Metzger A K, Herman M, McKnite S, Tang W, Yannopoulos D. Improved cerebral perfusion pressures and 24-hr neurological survival in a porcine model of cardiac arrest with active compression-decompression cardiopulmonary resuscitation and augmentation of negative intrathoracic pressure. Crit Care Med. 2012; 40(6):1851-6. Epub 2012/04/11. doi: 10.1097/CCM.0b013e318246b9ad. PubMed PMID: 22487997; PubMed Central PMCID: PMCPMC3741964.

24. Friess S H, Sutton R M, French B, Bhalala U, Maltese M R, Naim M Y, et al. Hemodynamic directed CPR improves cerebral perfusion pressure and brain tissue oxygenation. Resuscitation. 2014; 85(9):1298-303. Epub 2014/06/20. doi: 10.1016/j.resuscitation.2014.05.040. PubMed PMID: 24945902; PubMed Central PMCID: PMCPMC4138228.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for resuscitation of the heart in a subject in need thereof, comprising intra-arterially, intravenously, or intra-osseosly administering to the subject suffering from cardiac arrest a therapeutically effective amount of a solution comprising polyethylene glycol (PEG) having a molecular weight of 8-100 kDa.

2. The method of claim 1, wherein the PEG has a molecular weight of 20 kDa.

3. The method of claim 1, wherein the solution comprises 5-30% PEG.

4. The method of claim 1, wherein the solution further comprises 0.1-10% of a PEG having a molecular weight of 1-10 kDa.

5. The method of claim 1, wherein the solution is administered to the femoral arterty.

6. The method of claim 1, wherein the solution is administered at a rate of less than 5% estimated blood volume per minute.

7. The method of claim 6, wherein the solution is administered for 1-10 minutes.

8. The method of claim 1, wherein the solution is administered during and/or after the administration of cardiopulmonary resuscitation (CPR).

9. The method of claim 1, wherein epinephrine is not co-administered to the subject.

10. The method of claim 1, wherein the subject suffers from one or more of myocardial infarction, cardiogenic shock, and non-cardiogenic shock.

* * * * *